United States Patent [19]
Archibald et al.

[11] Patent Number: 5,649,542
[45] Date of Patent: *Jul. 22, 1997

[54] CONTINUOUS NON-INVASIVE BLOOD PRESSURE MONITORING SYSTEM

[75] Inventors: G. Kent Archibald, Vadnais Heights; Timothy G. Curran, Ramsey; Orland H. Danielson, Roseville; Marius O. Poliac, St. Paul; Roger C. Thede, Minnneapolis, all of Minn.

[73] Assignee: Medwave, Inc., Arden Hills, Minn.

[*] Notice: The term of this patent shall not extend beyond the expiration date of Pat. No. 5,450,852.

[21] Appl. No.: 434,264

[22] Filed: May 3, 1995

Related U.S. Application Data

[63] Continuation of Ser. No. 150,382, Nov. 9, 1993, abandoned.

[51] Int. Cl.$^6$ .................................................. A61B 5/02
[52] U.S. Cl. ........................................ 128/681; 128/690
[58] Field of Search ................................ 128/672, 677, 128/678–690

[56] References Cited

U.S. PATENT DOCUMENTS

| | | | |
|---|---|---|---|
| 4,260,951 | 4/1981 | Lewyn | 128/690 X |
| 4,307,727 | 12/1981 | Haynes | 128/672 |
| 4,664,126 | 5/1987 | Link . | |
| 4,699,151 | 10/1987 | Link . | |
| 4,712,563 | 12/1987 | Link . | |
| 4,799,491 | 1/1989 | Eckerle . | |
| 4,830,017 | 5/1989 | Perry et al. | 128/672 |
| 4,928,702 | 5/1990 | Cousin | 128/678 |
| 5,025,792 | 6/1991 | Hon et al. | 128/690 X |
| 5,033,471 | 7/1991 | Yokoe et al. | 128/681 |
| 5,238,000 | 8/1993 | Niwa | 128/690 X |
| 5,240,007 | 8/1993 | Pytel et al. | 128/690 X |
| 5,247,944 | 9/1993 | Hirano et al. | 128/687 X |
| 5,284,150 | 2/1994 | Butterfield et al. | 128/687 X |
| 5,450,852 | 9/1995 | Archibald et al. | 128/687 X |

*Primary Examiner*—Lee S. Cohen
*Assistant Examiner*—Samuel Gilbert
*Attorney, Agent, or Firm*—Kinney & Lange, P.A.

[57] ABSTRACT

A sensor for sensing blood pressure within an underlying artery as the underlying artery is compressed includes a transducer and a compressible sidewall. The transducer senses blood pressure of blood pressure pulses as the pulses travel beneath the sensor. As each blood pressure pulses crosses an edge of the sensor, each pulse exerts a force on the sensor in a direction parallel to the underlying artery. Tissue surrounding the underlying artery also exerts a force. The compressible sidewall is distant from the transducer and engages tissue surrounding the underlying artery. The compressible side wall neutralizes the force exerted by the tissue surrounding the underlying artery and dampens the force parallel to the underlying artery so that a substantially zero pressure gradient exists across the transducer.

45 Claims, 4 Drawing Sheets

CONTINUOUS NON-INVASIVE BLOOD PRESSURE MONITORING SYSTEM

This is a file wrapper continuation of application Ser. No. 08/150,382, filed Nov. 9, 1993 now abandoned.

BACKGROUND OF THE INVENTION

The present invention relates to systems for measuring arterial blood pressure. In particular, the invention relates to a sensor assembly for measuring arterial blood pressure in a relatively continuous and non-invasive manner.

Blood pressure has been typically measured by one of four basic methods: invasive, oscillometric, auscultatory and tonometric. The invasive method, otherwise known as an arterial line (A-Line), involves insertion of a needle into the artery. A transducer connected by a fluid column is used to determine exact arterial pressure. With proper instrumentation, systolic, mean and diastolic pressure may be determined. This method is difficult to set up, is expensive and involves medical risks. Set up of the invasive or A-line method poses problems. Resonance often occurs and causes significant errors. Also, if a blood clot forms on the end of the catheter, or the end of the catheter is located against the arterial wall, a large error may result. To eliminate or reduce these errors, the set up must be adjusted frequently. A skilled medical practitioner is required to insert the needle into the artery. This contributes to the expense of this method. Medical complications are also possible, such as infection or nerve damage.

The other methods of measuring blood pressure are non-invasive. The oscillometric method measures the amplitude of pressure oscillations in an inflated cuff. The cuff is placed against a cooperating artery of the patient and thereafter pressurized to different levels. Mean pressure is determined by sweeping the cuff pressure and determining the mean cuff pressure at the instant the peak amplitude occurs. Systolic and diastolic pressure is determined by cuff pressure when the pressure oscillation is at some predetermined ratio of peak amplitude.

The auscultatory method also involves inflation of a cuff placed around a cooperating artery of the patient. Upon inflation of the cuff, the cuff is permitted to deflate. Systolic pressure is indicated when Korotkoff sounds begin to occur as the cuff is deflated. Diastolic pressure is indicated when the Korotkoff sounds become muffled or disappear. The auscultatory method can only be used to determine systolic and diastolic pressures.

Because both the oscillometric and the auscultatory methods require inflation of a cuff, performing frequent measurements is difficult. The frequency of measurement is limited by the time required to comfortably inflate the cuff and the time required to deflate the cuff as measurements are made. Because the cuff is inflated around a relatively large area surrounding the artery, inflation and deflation of the cuff is uncomfortable to the patient. As a result, the oscillometric and the auscultatory methods are not suitable for long periods of repetitive use.

Both the oscillometric and auscultatory methods lack accuracy and consistency for determining systolic and diastolic pressure values. The oscillometric method applies an arbitrary ratio to determine systolic and diastolic pressure values. Similarly, the auscultatory method requires a judgment to be made as to when the Korotkoff sounds start and when they stop. This detection is made when the Korotkoff sound is at its very lowest. As a result, the auscultatory method is subject to inaccuracies due to low signal-to-noise ratio.

The fourth method used to determine arterial blood pressure has been tonometry. The tonometric method typically involves a transducer including an array of pressure sensitive elements positioned over a superficial artery. Hold down forces are applied to the transducer so as to flatten the wall of the underlying artery without occluding the artery. The pressure sensitive elements in the array typically have at least one dimension smaller than the lumen of the underlying artery in which blood pressure is measured. The transducer is positioned such that at least one of the individual pressure sensitive elements is over at least a portion of the underlying artery. The output from one of the pressure sensitive elements is selected for monitoring blood pressure. The pressure measured by the selected pressure sensitive element is dependent upon the hold down pressure used to press the transducer against the skin or the patient. These tonometric systems measure a reference pressure directly from the wrist and correlate this with arterial pressure. However, a patient moves, recalibration of the tonometric system is required because the system may experience a change in gains. Because the accuracy of these tonometric systems depends upon the accurate positioning of the individual pressure sensitive element over the underlying artery, placement of the transducer is critical. Consequently, placement of the transducer with these tonometric systems is time-consuming and prone to error.

The oscillometric, auscultatory and tonometric methods measure and detect blood pressure by sensing force or displacement caused by blood pressure pulses as the underlying artery is compressed or flattened. The blood pressure is sensed by measuring forces exerted by blood pressure pulses in a direction perpendicular to the underlying artery. However, with these methods, the blood pressure pulse also exerts forces parallel to the underlying artery as the blood pressure pulses cross the edges of the sensor which is pressed against the skin overlying the underlying artery of the patient. In particular, with the oscillometric and the auscultatory methods, parallel forces are exerted on the edges or sides of the cuff. With the tonometric method, parallel forces are exerted on the edges of the transducer. These parallel forces exerted upon the sensor by the blood pressure pulses create a pressure gradient across the pressure sensitive elements. This uneven pressure gradient creates at least two different pressures, one pressure at the edge of the pressure sensitive element and a second pressure directly beneath the pressure sensitive element. As a result, the oscillometric, auscultatory and tonometric methods produce inaccurate and inconsistent blood pressure measurements.

SUMMARY OF THE INVENTION

The present invention is an improved sensor and method for measuring blood pressure within an underlying artery. A sensor for sensing blood pressure within an underlying artery as the underlying artery is compressed includes a transducer and a compressible sidewall. The transducer senses blood pressure of blood pressure pulses as the pulses travel beneath the sensor. As each blood pressure pulse crosses an edge of the sensor, each pulse exerts a force on the sensor in a direction parallel to the underlying artery. The compressible sidewall dampens the force parallel to the underlying artery so that a substantially zero pressure gradient exists across the transducer. The compressible side wall also forces tissue surrounding the artery to a neutral position so that the pressure of the artery can be measured.

DETAILED DESCRIPTION OF THE PREFERRED EMBODIMENTS

Figure 1:
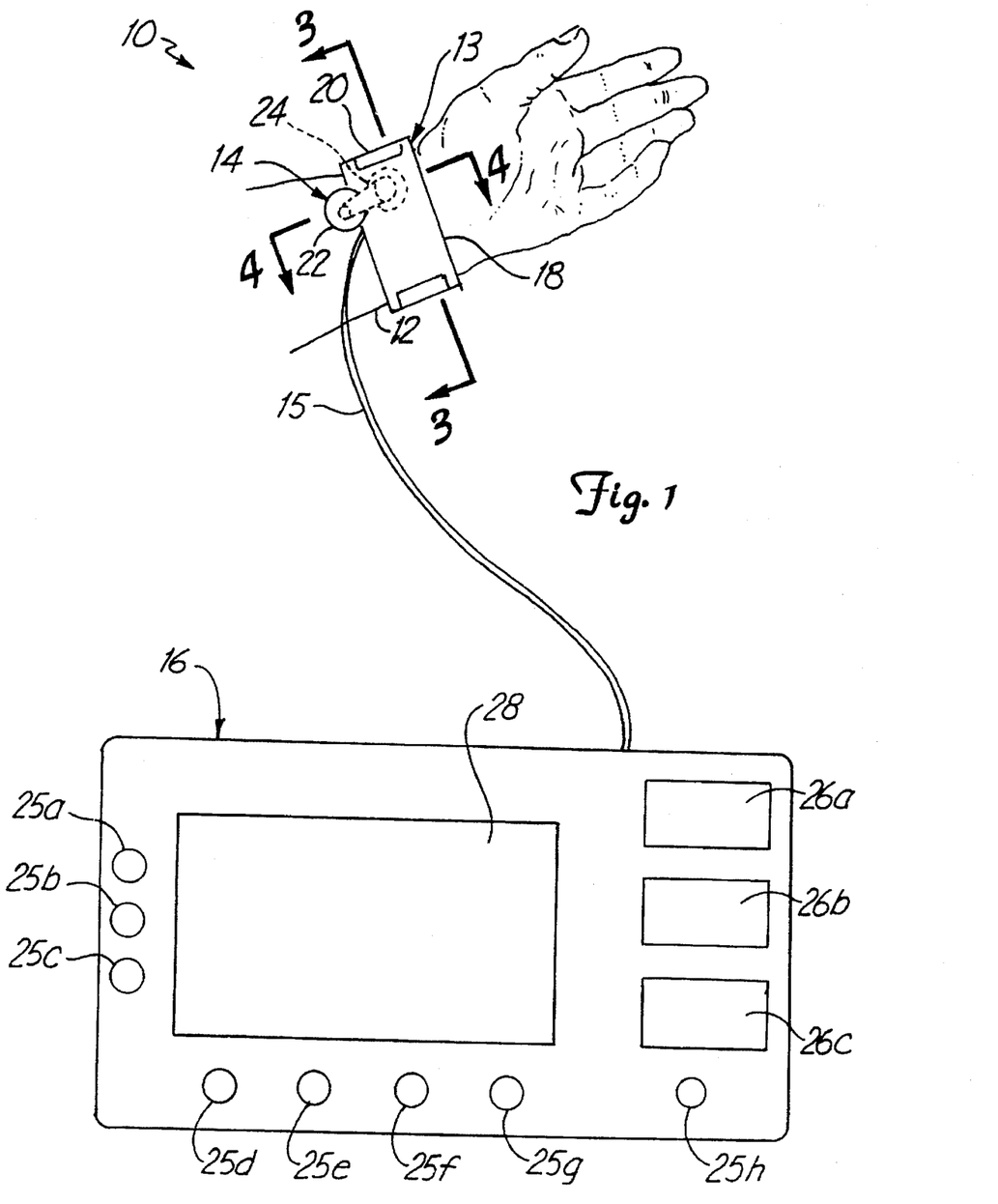
FIG. 1 is a perspective view of a blood pressure monitoring system having a sensor assembly mounted to the wrist of a patient.

FIG. 1 shows a blood pressure monitoring system 10 for measuring and displaying blood pressure within an underlying artery (not shown) within wrist 12 of a patient. Monitoring system 10 includes wrist assembly 13, sensor assembly 14, cable 15 and monitor 16.

Wrist assembly 13 includes sensor support 18 and strap 20. Sensor support 18 fits over wrist 12 above an underlying artery (not shown) and supports sensor assembly 14 over the underlying artery. Sensor support 18 is preferably rigid.

Strap 20 comprises a flexible band and is preferably made of nylon. Strap 20 latches to sensor support 18 and wraps around wrist 12 to maintain sensor assembly 14 on wrist 12.

Sensor assembly 14 is electrically coupled to monitor 16 through cable 15 and generally includes motor assembly 22 and sensor 24. Motor assembly 22 is coupled to sensor support 18 and is mechanically coupled to sensor 24. Motor assembly 22 applies a variable hold down pressure to sensor 24 so that blood pressure can be sensed and measured as varying hold down pressures are applied to the underlying artery by sensor assembly 14.

Sensor 24 is coupled to motor assembly 22. When placed on wrist 12, sensor 24 is positioned over the underlying artery. Sensor 24 senses and measures blood pressure pulses within the underlying artery.

Monitor 16 is coupled to motor assembly 22 and to sensor 24 by cable 15. Monitor 16 includes control switches or various inputs 25a–25h, digital displays 26a–26c, and display screen 28. Inputs 25a–25h control monitor 16 and permit monitor 16 to be calibrated. Inputs 25a–25c comprise hard keys for controlling monitor 16. Inputs 25d–25h consist of software programmable keys which are adaptable for various functions. Digital displays 26a–26c continually display systolic, diastolic and mean blood pressure, respectively. Display screen 28 displays the blood pressure pulse, waveforms and prompts to guide the operator. Monitor 16 receives the sensed blood pressure pulse signals taken by sensor 24 and calculates the systolic, diastolic and mean blood pressures. Once these values are determined, monitor 16 displays the corresponding values in both analog and digital form. Monitor 16 also controls motor assembly 22.

In operation, sensor 24 is strapped to wrist 12 over the radial artery. Motor assembly 22 moves sensor 24 to vary the pressure applied to wrist 12 above the radial artery. As this pressure is varied, an arterial pressure waveform is sensed. An arterial pressure waveform or shape is obtained by measuring amplitude of pressure versus time of an individual cardiac cycle. The shape of the waveform is a function of the applied pressure and is used by digital signal processing circuitry of monitor 16 to calculate systolic, mean and diastolic pressure. The calculated pressures are displayed by displays 26a–26c and display screen 28.

Figure 2:
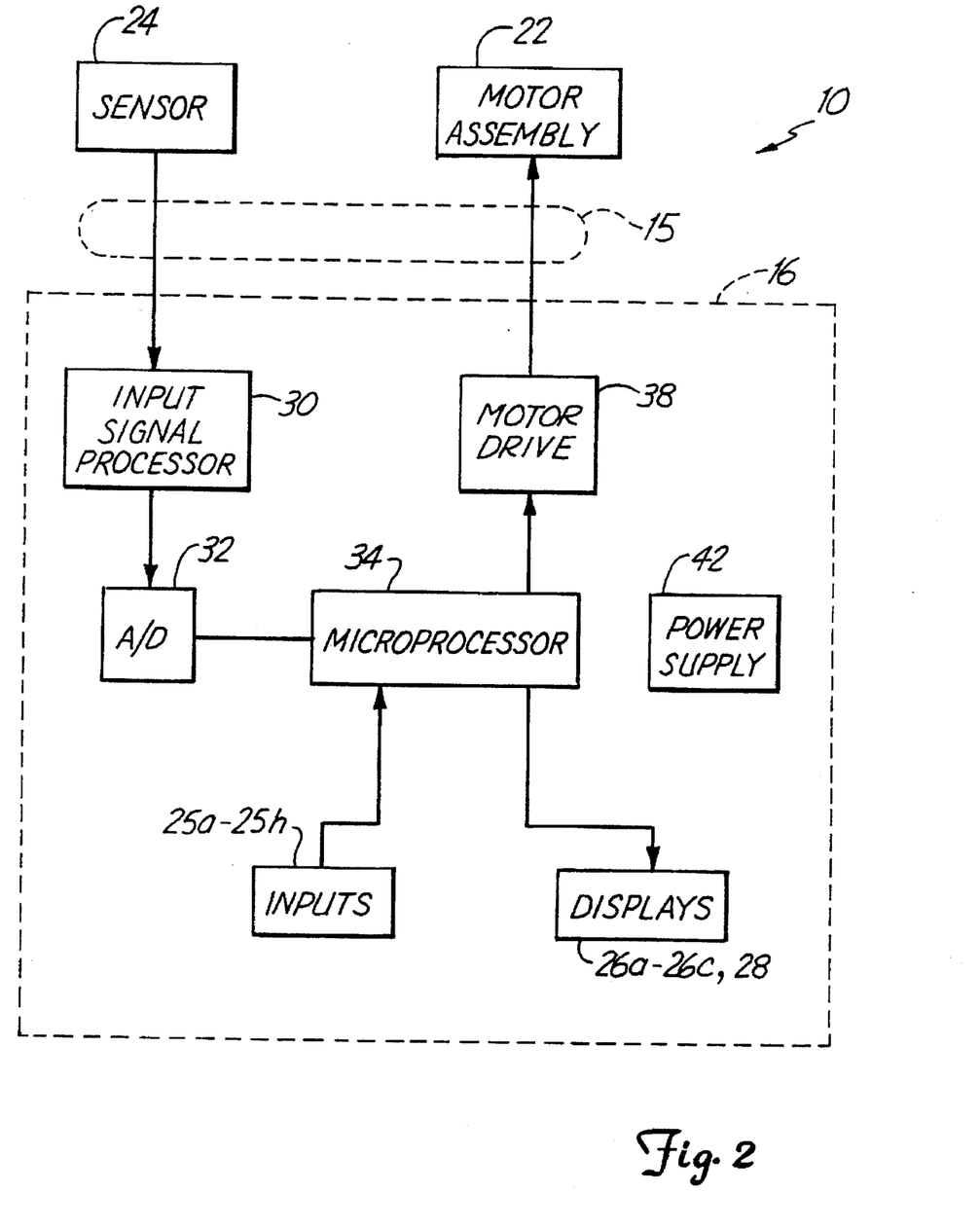
FIG. 2 is a block diagram of the blood pressure monitoring system of FIG. 1.

FIG. 2 shows a block diagram of blood pressure monitoring system 10. As best shown by FIG. 2, monitor 16 further includes input signal processor 30, analog-to-digital converter 32, microprocessor 34, inputs 25a–25h, motor drive 38, displays 26a–26c and 28, and power supply 42. In operation, microprocessor 34 receives inputted signals from inputs 25a–25h. Inputs 25a–25h may also consist of a keyboard or other input mechanisms. Inputs 25a–25h permit microprocessor 34 to be calibrated.

Microprocessor 34 controls motor drive 38 to vary hold down pressure applied by motor assembly 22 on sensor 24. Hold down pressure is applied to the anatomy of the patient directly above the artery by sensor 24. The hold down pressure applied by motor assembly 22 on sensor 24 is increased over time. As the force or hold down pressure applied by sensor 24 increases, the amplitude of the blood pressure pulse also increases until a maximum amplitude results. Once the maximum amplitude of maximum energy transfer results, the amplitude of the blood pressure pulse begins to decrease as the artery begins to flatten out beyond the point of maximum energy transfer.

Sensor 24 senses and detects the amplitude and shape of the blood pressure pulses within the underlying artery. Sensor 24 creates electric sensor signals representing the amplitude of the sensed blood pressure pulses. The sensor signals are transmitted to input signal processor 30 of monitor 16. Input signal processor 30 processes the sensor signals and filters any unwanted or undesirable noise and other effects. The sensor signals are then transmitted from input signal processor 30 to analog-to-digital convertor 32. Analog-to-digital convertor 32 converts the sensor signal into digital form. A digital signal representing the amplitude of the sensed blood pressure pulses is sent to microprocessor 34.

Based upon the digital sensor signals representing the sensed amplitude and shape of the blood pressure pulses, microprocessor 34 determines wave shape information by measuring amplitude and shape versus time of individual cardiac cycles. The arterial wave shape information is determined by sampling the arterial waves at a rate significantly above heart rate so that a good definition of the arterial pressure wave is measured. From this information, microprocessor 34 calculates systolic, diastolic and mean blood pressures. When no pressure gradient exists across the face of sensor 24, the hold down pressure corresponding to the cardiac cycle having the peak pressure amplitude or the maximum energy transfer is substantially equal to the mean arterial pressure. Based upon the mean arterial pressure, microprocessor 34 calculates systolic and diastolic blood pressure.

In the alternative, microprocessor 34 calculates blood pressure from the relationship between the pressure amplitude of the individual cardiac waveform and the applied hold down pressure of sensor 24. These results may be derived from waveforms both before and after the waveform that has maximum energy transfer.

In addition, microprocessor 34 may also calculate blood pressure from the shape of individual cardiac waveforms. These results are based on the area under part of the waveforms or they may be based on the shape of a rise time on any number of parameters. The calculated blood pressures are displayed on displays 26a–26c. Power supply 42 provides power to monitor 16 and motor assembly 22.

Figure 3:
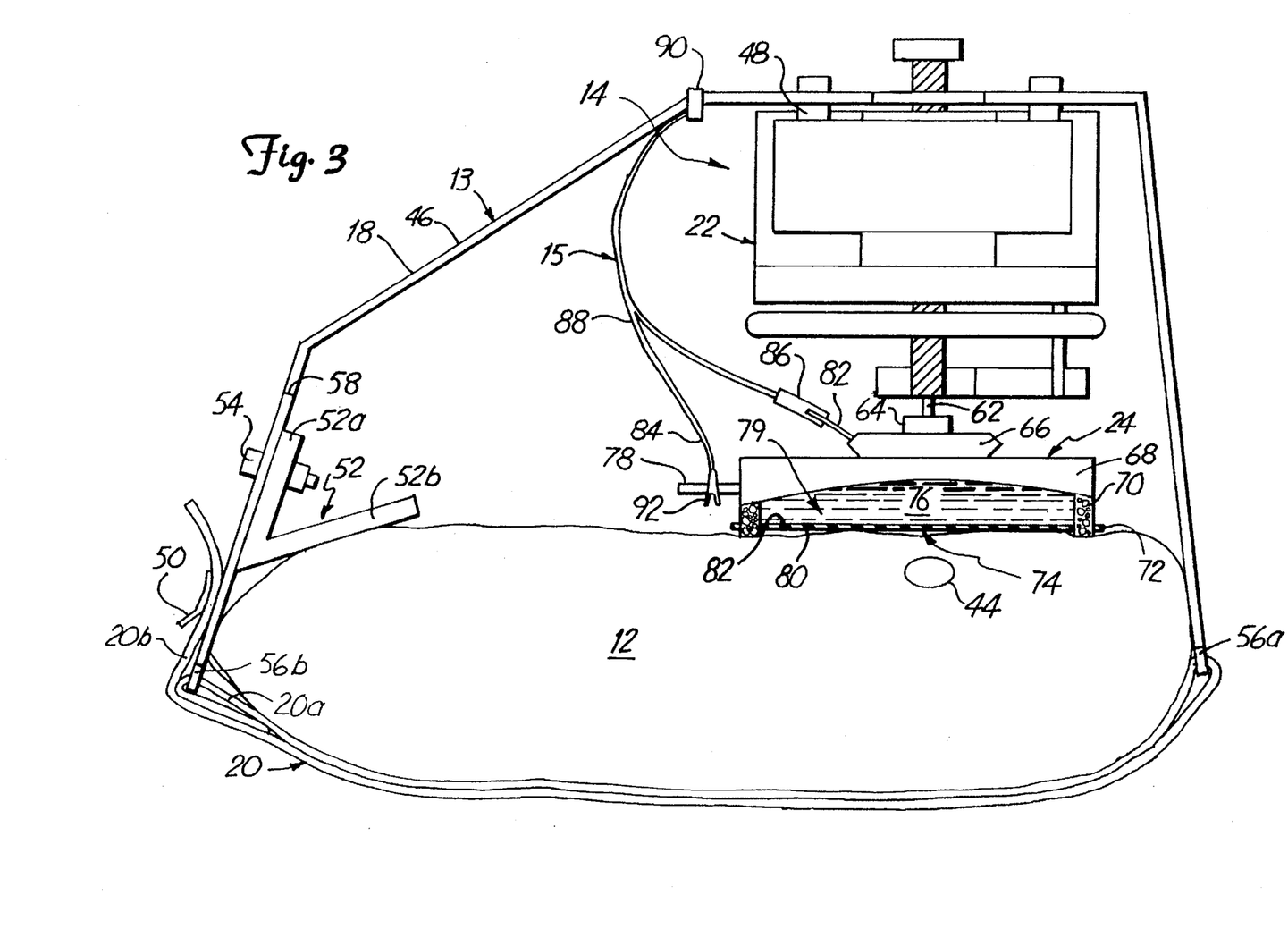
FIG. 3 is a cross-sectional view of the sensor assembly of FIG. 1 mounted to the wrist of the patient.

FIG. 3 is a cross-sectional view taken along lines 3—3 of FIG. 1, showing wrist assembly 13 and sensor assembly 14 placed upon wrist 12 of a patient having an underlying artery 44. FIG. 3 shows sensor support 18 and strap 20 of wrist assembly 13 and sensor 24 of sensor assembly 14 in greater detail. Sensor support 18 includes frame 46, spacer 48, latch 50, stabilizing support 52 and screw 54. Frame 46 is a metal frame bent to partially surround wrist 12. Frame 46 includes lower strap holes 56a, 56b and adjustment slot 58. Strap holes 56a, 56b are located along the lower end of frame 46. Strap hole 56b permits end loop 20a of strap 20 to be secured to frame 46. Strap 20 is fed through strap hole 56a so that strap 20 is doubled back and free end 20b is attached to latch 50. Adjustment slot 58 extends upward from above strap hole 56b toward a top end of frame 46. Adjustment slot 58 permits stabilizing support 52 to be moved up and down within slot 58 so that stabilizing support 52 may be adjusted for the particular anatomy to which sensor assembly 14 is being secured. Frame 46 supports motor assembly 22 and sensor 24 above underlying artery 44 of wrist 12. Frame 46 also supports strap 20 below wrist 12. As a result, sensor 24 is held in a stable position with respect to wrist 12 while blood pressure pulses are being sensed and measured.

Spacer 48 is mounted along a top horizontal portion of frame 46 and is positioned between sensor assembly 14 and frame 46. Spacer 48 spaces sensor assembly 14 from frame 46.

Latch 50 is fixedly coupled to frame 46 between strap hole 56b and adjustment slot 58. Latch 50 releasably secures free end 20b of strap 20 to frame 46 so that wrist 12 is supported and positioned between frame 46, sensor 24 and strap 20.

Stabilizing support 52 generally consists of a V-shaped bar having a first leg 52a extending parallel to adjustment slot 58 of frame 46 and having a second leg 52b extending over and above wrist 12. Stabilizing support 52 is slidably secured to frame 46 by screw 54. Screw 54 extends through first leg 52a and adjustment slot 58. Screw 54 and slot 58 cooperate to permit stabilizing support 52 to be vertically positioned with respect to wrist 12. Thus, second leg 52b of stabilizing support 52 holds wrist 12 down against strap 20 to limit movement of wrist 12 while blood pressure pulses within underlying artery 44 are being sensed and measured.

Strap 20 consists of an elongate flexible band. Strap 20 has a first end looped through strap hole 56b and secured to itself to form end loop 20a. Strap 20 has second free end 20b which is fed through strap hole 56a and doubled back below wrist 12 to latch 50 where free end 20b is latched and releasably secured to frame 46 by latch 50. Strap 20 supports wrist 12 in position below frame 46 and sensor 24.

Also as best shown by FIG. 3, sensor 24 is coupled to cable 15 and includes pivot block pin 62, pivot block 64, transducer 66, flange 68, sidewall 70, restraining ring 72, diaphragm 74, pressure or fluid coupling medium 76 and fluid gel port 78. Pivot block pin 62 has a first end coupled to pivot block 64 and a second end which is coupled to motor assembly 22. Pivot block pin 62 couples sensor 24 to motor assembly 22.

Pivot block 64 receives the first end of pivot block pin 62. Pivot block 64 has a lower end which is coupled to transducer 66. Pivot block 64 couples sensor 24 to motor assembly 22.

Transducer 66 is disc-shaped. Transducer 66 is coupled between pivot block 64 and flange 68. Transducer 66 contains a pressure-sensitive element such as a piezoresistive sensor bridge (not shown) for sensing blood pressure pulses within artery 44.

Flange 68 is ring-shaped and is slightly concave so that sensor 24 better conforms to the anatomy or shape of wrist 12. Flange 68 is fixedly coupled around an outer perimeter of transducer 60. Flange 68 supports side wall 70 and couples side wall 70 to transducer 66.

Side wall 70 is ring shaped and compressible, and is coupled to a lower surface of flange 68. Side wall 70 is distant from transducer sensing elements (not shown) of transducer 66, yet engages tissue surrounding artery 44 to support transducer 66 above artery 44 and above tissue surrounding artery 44. As a result, the exact positioning of transducer 66 over artery 44 is not required. At the same time, side wall 70 is not so distant from transducer 66 so as to surround a large enough area of tissue surrounding artery 44 to cause discomfort to the patient. Because sidewall 70 separates transducer 66 from the tissue surrounding artery 44, blood pressure measurement errors caused by inadvertent patient movement are lessened.

In addition, sidewall 70 creates a substantially zero pressure gradient across sensor 24 so that sensor 24 more accurately measures blood pressure. Sidewall 70 is constrained from expanding outward in a planar direction away from the outer perimeter of transducer 66. Because side wall 70 is compressible, side wall 70 dampens and absorbs threes or pressure exerted by blood pressure pulses as the pulses cross side wall 70 along the perimeter or edge of sensor 24. Side wall 70 also applies force to tissue surrounding artery 44. The force applied by side wall 70 substantially equals force exerted by the tissue surrounding artery 44 to offset or neutralize the force exerted from the tissue. As a result, the force applied by side wall 70 presses the tissue to a neutral position so the pressure of artery 44 can be more accurately measured. The force of side wall 70 that is applied to the tissue surrounding artery 44 is coupled to flange 68. Flange 68 is coupled to transducer 66, but is not coupled to transducer sensing elements (not shown) of transducer 66. Thus, the force applied by side wall 70 which is used to press the tissue to a neutral position is not sensed by the transducer sensing elements of transducer 66. This neutralizing effect of sensor 24 allows blood pressure monitoring system 10 to more accurately measure the arterial pressure of artery 44 without inaccuracies introduced by forces from the surrounding tissue. Consequently, side wall 70 reduces or eliminates uneven pressure gradients within fluid coupling medium 76 across sensor 24 to create a substantially zero pressure gradient across sensor 24. As a result, sensor 24 more consistently and more accurately measures blood pressure. Preferably, side wall 70 is formed from closed cell foam. Alternatively, side wall 70 may be formed from open cell foam or other compressible materials or structural designs.

Because side wall 70 is compressible side wall 70 better conforms to the anatomy or shape of wrist 12. However, because side wall 70 is constrained from expanding outward, side wall 70 does not stretch diaphragm 74 when being pressed against wrist 12. By preventing tension across diaphragm 74, sensor 24 further eliminates pressure gradients across transducer 66, which results in more accurate and consistent blood pressure readings.

Restraining ring 72 normally consists of a flexible ring made of fiber or other similar material. Restraining ring 72 encircles side wall 70 and further prevents side wall 70 from expanding outward in a direction away from the outer perimeter of transducer 66.

Diaphragm 74 is preferably formed from a thin flexible polymer or rubber. Diaphragm 74 extends across side wall 70 to form chamber 79 in front of transducer 66. Diaphragm 74 is preferably positioned across side wall 70 so as to be like of tension. Diaphragm 74 transmits blood pressure pulses from a first side 80 to a second side 82 within chamber 79.

Fluid coupling medium 76 preferably is a gel, although fluid coupling medium 76 may consist of any fluid or liquid capable of transmitting pressure from diaphragm 74 to transducer 66. Fluid coupling medium 76 is contained within chamber 79 between diaphragm 74, side wall 70, flange 68 and transducer 66. Fluid coupling medium 76 interfaces between diaphragm 74 and transducer 66 and transmits the blood pressure pulses from surface 82 of diaphragm 74 to Transducer 66.

Sensor 24 continuously and accurately senses blood pressure pulses within the underlying artery. Because sidewall 70 is compressible sensor 24 dampens force, a parallel to the underlying artery which are extended upon sensor 24 by blood pressure pulses crossing beneath the edge of sensor 24. In addition, sensor 24 better conforms to the anatomy of wrist 12. Because sidewall 70 and diaphragm 74 are constrained from expanding outward and are free of tension, pressure gradients across transducer 66 arc eliminated. Moreover, sensor 24 also neutralizes the tissue surrounding artery 44. Consequently, more accurate and consistent blood pressure readings arc taken. Moreover, sidewall 70, diaphragm 74 and fluid coupling medium 76 form a large sensing area through which blood pressure pulses may be transmitted to transducer 66. As a result, sensor 24 is not as dependent upon accurate positioning of transducer 66 over the underlying artery. Sensor 24 quickly and accurately provides a continuous measurement of blood pressure over long periods of use without discomfort to the patient.

Fluid port 78 extends into flange 68 and communicates with chamber 79. Port 78 permits chamber 79 to be filled with fluid coupling medium 76.

Cable 15 electrically couples sensor 24 to the monitor 16. Cable 15 includes transducer leads 83, ground wire 84, connector 86, cable 88 and clamp 90. Transducer leads 83 consists of wires electrically coupled to transducer 66. Transducer leads 83 transmits signals representing the sensed blood pressure pulses from transducer 66.

Grounding wire 84 consists of a wire having a ground, clip 92 at one end. Grounding clip 92 mounts onto fluid port 78. An opposite end of grounding wire 84 is electrically coupled to cable 88. Grounding wire 84 electrically grounds sensor assembly 24.

Connector 86 electrically couples transducer leads 83 to cable 88. Cable 88 has first end coupled to connector 88 and a second end which is coupled to monitor 16 (shown in FIG. 1). Cable 88 permits sensor 24 to transmit signals representing the sensed blood pressure pulses to monitor 16 where the signals are measured. Clamp 90 couples cable 88 to frame 46 of sensor support 18 and relieves strain within cable 88.

Figure 4:
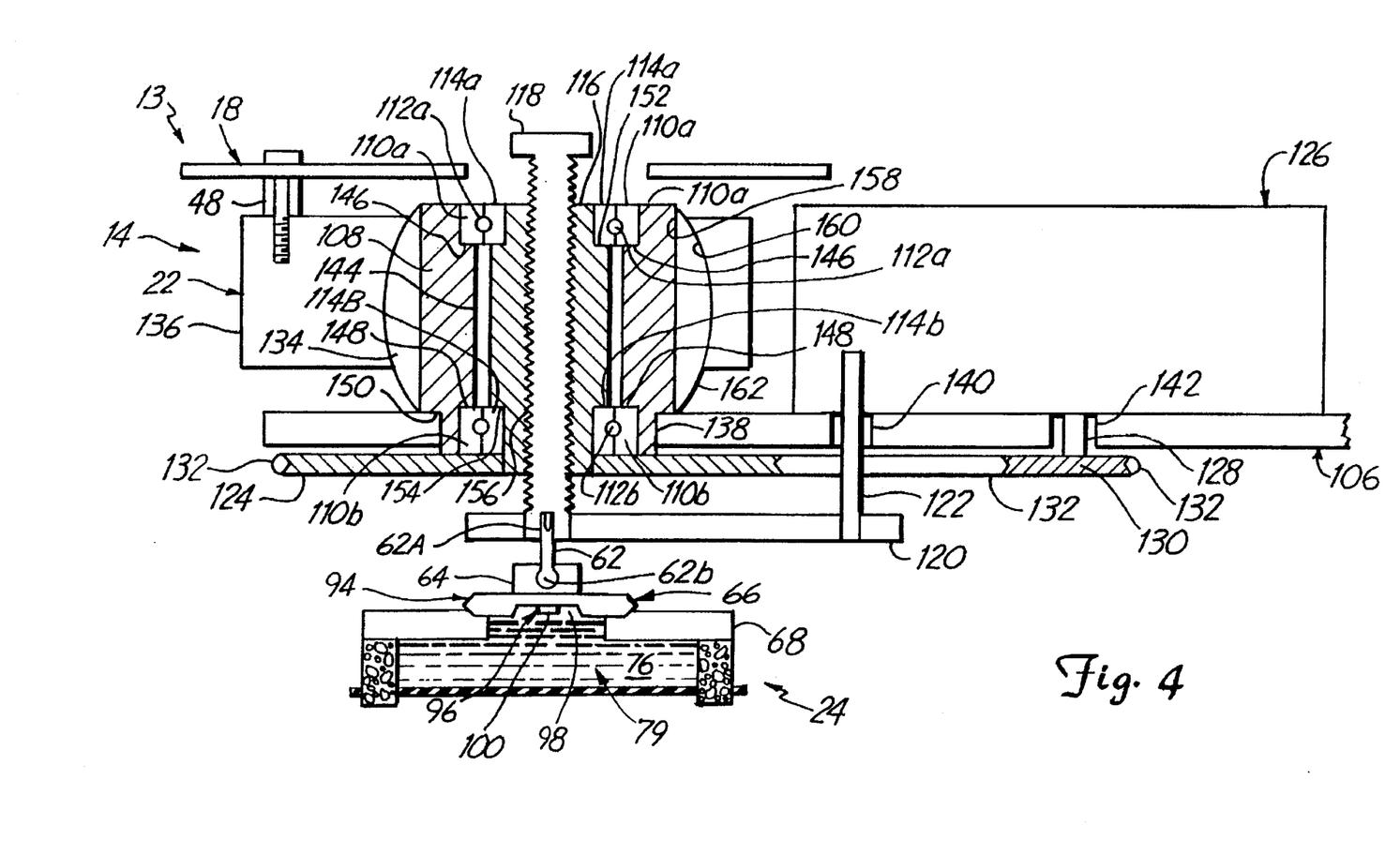
FIG. 4 is a cross-sectional view of the sensor assembly of FIG. 1.

FIG. 4 is a cross-sectional view of sensor assembly 14 and sensor support 18 of wrist assembly 13 taken along lines 4—4 of FIG. 1. FIG. 4 shows sensor 24 and motor assembly 22 in greater detail. Portions of sensor support 18 are omitted for clarity. FIG. 4 best shows pivot block pin 62 and pivot block 64 of sensor 24. As shown in FIG. 4, upper end 62a of pivot block pin 62 is bifurcated and is frictionally coupled to motor assembly 22. Because pivot block pin 62 is bifurcated, the diameter of pivot block pin 62 may be enlarged or reduced. As a result, pivot block pin 62 and sensor 24 may be remote removed from motor assembly 22 without the use of tools by compressing pivot block pin 62 to reduce its diameter. Pivot block 64 includes a cavity for receiving the lower end 62b of pivot block pin 62. Pivot block 64 rotates or pivots about lower end 62b of pivot block pin 62 to prevent accurate orientation of sensor 24.

As best shown by FIG. 4, transducer 66 is generally disc-shaped and includes transducer holder 94 and transducer clement 96. Transducer holder 94 includes central bore 98 extending into a lower end of transducer holder 94. Transducer holder 94 has a top end which is coupled to pivot block 64. The lower end of transducer holder 94 is fixedly secured to flange 68. Transducer element 96 is supported and mounted within bore 98 of transducer holder 94.

Transducer element 96 is well known in the art and includes sensing surface 100. Sensing surface 100 is preferably sensitive to pressure changes within chamber 79 transmitted through fluid coupling medium 76. Transducer element 96 is positioned within bore 98 of transducer holder 94 so that sensing surface 100 of transducer element 96 faces downward out of bore 98. Transducer element 96 preferably comprises a piezoresistive sensor bridge. Transducer element 96 senses blood pressure pulses from an underlying artery of a patient.

Motor assembly 22 presses sensor 24 against skin overlying the underlying artery so that the amplitudes of blood pressure pulses may be sensed over a range of various hold down pressures. As best shown by FIG. 4, motor assembly 22 includes base plate 106, outer sleeve 108, upper and lower outer races 110a and 110b, bearing balls 112a and 112b, upper and lower inner races 114a and 114b, inner sleeve 116, threaded screw shaft 118, stop arm 120, stop shaft 122, drive pulley 124, motor 126, drive shaft 128, motor pulley 130, drive belt 132, ball 134 and socket 136.

Base plate 106 is an elongate flat rigid plate which includes sleeve hole 138, stop shaft hole 140 and drive shaft hole 142. Sleeve hole 138 has a diameter large enough to permit outer sleeve 108. After sleeve 116 and screw shaft 118 to extend through sleeve hole 138. Stop shaft hole 140 has a diameter large enough to permit stop shaft 122 to extend through stop shaft hole 140. Drive shaft hole 142 permits drive shaft 128 to couple motor 126 to motor pulley 130.

Outer sleeve 108 is generally cylindrical and includes bore 144, upper inside shoulder 146, lower inside shoulder 148, and lower outside shoulder 150. Bore 144 extends through outer sleeve 108. Towards a top end and a bottom end of outer sleeve 108, bore 144 widens to to form upper inside shoulder 146 and lower inside shoulder 148, respectively. Toward a lower end of outer sleeve 108, an outer diameter of sleeve 108 narrows to form lower outside shoulder 150. Lower outside shoulder 150 engages sleeve hole 138 of base plate 106 and fixedly couples outer sleeve 108 to base plate 106. Upper inside shoulder 146 and lower inside shoulder 148 support outer races 110. Inside races 114 are coupled to inner sleeve 116. Inner races 110 and outer races 114 cooperate to support an annular array of bearing balls 112 therebetween. As a result, outer sleeve 108 rotatably supports inner sleeve 116.

Inner sleeve 116 is cylindrical in shape and includes upper outside shoulder 152, lower outside shoulder 154 and threaded inner bore 156. Towards an upper end and a lower end of inner sleeve 116, an outer diameter narrows to form upper outside shoulder 152 and lower outside shoulder 154, respectively. Shoulders 152 and 154 support inner races 114a and 114b, respectively. Threaded inner bore 156 extends through inner sleeve 156 and receives threaded screw shaft 118.

Threaded screw shaft 118 extends through threaded bore 156 of inner sleeve 116. The lower end of threaded screw shaft 118 receives an upper end of pivot block pin 62. Consequently, threaded screw shaft 118 is coupled to and supports sensor 24. Threaded screw shaft 118 is further coupled to stop arm 120.

Stop arm 120 generally consists of an elongate arm having a first end fixedly coupled to a lower end of threaded screw shaft 118 and having a second end fixedly coupled to a lower end of stop shaft 122. Stop shaft 122 extends upward from stop arm 120 through stop shaft hole 140 of base plate 106. Stop arm 120 and stop shaft 122 prevent threaded screw shaft 118 from rotating. At the same, stop arm 120 and stop shaft 122 permit threaded screw shaft 118 to move up and down. As a result, rotation of of inner sleeve 116 with respect to threaded screw shaft 118 causes threaded screw shaft 118 to to move up and down as the threads of threaded screw shaft 118 engage the threads of inner sleeve 116. Because sensor 24 is coupled to threaded screw shaft 118, movement of threaded screw shaft 118 up and down causes sensor 24 to vary pressure applied to skin above the underlying artery. As pressure is varied, an arterial pressure wave form is generated which is measured by transducer 66 of sensor 24.

Drive pulley 124 generally consists of a circular pulley. Drive pulley 124 has a groove along its outer perimeter sized to accommodate drive belt 132. Drive pulley 124 is fixedly secured to a lower end of inner sleeve 116 below base plate 106. Rotation of drive pulley 124 permits inner sleeve 116 to be rotated so that threaded screw shaft 118 is raised and lowered.

Motor 126 is fixedly coupled to base plate 106. Motor 126 drives drive shaft 128. Drive shaft 128 extends through drive shaft hole 142 and is coupled to motor pulley 130 below base plate 106. Motor pulley 130 is circular and has an outer groove along its perimeter sized to accommodate drive belt 132. Drive belt 132 generally consists of a band or belt. Drive belt 137 fits within the grooves of drive pulley 124 and motor pulley 130. Drive belt 132 partially encircles drive pulley 124 and motor pulley 130 to provide rotational communication between drive pulley 124 and motor pulley 130.

In operation, motor 126 rotates motor pulley 130, which in turn, rotates drive pulley 124 and inner sleeve 116. As a result, rotation of motor pulley 130 by motor 126 causes threaded screw shaft 118 to move up and down depending upon the rotational direction of motor pulley 130 and inner sleeve 116. By raising and lowering screw shaft 118 and sensor 24, motor 126 controls and continuously varies the hold down pressure applied to the skin above the underlying artery by sensor 24. This interaction between sensor 24 and the underlying artery permits blood pressure monitoring system 10 to better measure blood pressure.

Ball 134 includes central bore 158 and convex surface 160. Central bore 158 extends from a top end to a bottom end of ball 134. Central bore 158 permits outer sleeve 108 to be press-fit within ball 134. Convex surface 160 frictionally engages socket 136 to hold sensor assembly 14 in position. Convex surface 160 of ball 134 also permits sensor assembly 14 to be oriented in a proper position for accurate operation.

Socket 136 is generally rectangular and is coupled to frame 46 of sensor support 18. Socket 136 includes concave bore 162. Concave bore 162 engages convex surface 160 of ball 134 to guide the positioning of ball 134 within socket 136 so that sensor assembly 14 may be properly oriented during operation.

Sensor 24 provides continuous external measurements of blood pressure in an underlying artery. Because sensor 24 calculates blood pressure non-invasively, blood pressure is measured at a lower cost and without medical risks. In addition, sensor 24 provides continuous measurements of blood pressure. Because sensor 24 is relatively small compared to the larger cuffs used with the oscillometric and auscultatory methods, sensor 24 applies a hold down pressure to only a relatively small area above underlying artery of the patient. Consequently, blood pressure measurements may be taken with less discomfort to the patient. Because sensor 24 does not require inflation or deflation, continuous, more frequent measurements may be taken. At the same time, sensor 24 permits accurate and consistent calculation of blood pressure. Because the side wall, diaphragm and fluid coupling medium of sensor 24 forms a large sensing area through which blood pressure pulses may be transmitted to transducer 66, sensor 24 is not as dependent upon accurate positioning of transducer 66 over the underlying artery. Thus, sensor 24 is more tolerant to patient movement as measurements are being taken. Moreover, because the side wall of sensor 24 dampens and absorbs forces from the blood pressure pulses which are parallel to the underlying artery, uneven pressure gradients across transducer 66 are eliminated. The side wall of sensor 24 also presses tissue surrounding the artery to neutralize or offset forces exerted by the tissue. Consequently, sensor 24 senses blood pressure more consistently and more accurately.

Although the present invention has been described with reference to preferred embodiments, workers skilled in the art will recognize that changes may be made in form and detail without departing from the spirit and scope of the invention.

What is claimed is:

1. A sensor for measuring blood pressure pulses within an underlying artery surrounded by tissue of a patient as the underlying artery is compressed, the sensor comprising:

sensing means for sensing blood pressure of each pulse as each pulse travels beneath the sensor; and a variable height side wall distinct from and adjacent to the sensing means for engaging the tissue proximate the underlying artery and capable of conforming to the anatomy of the patient.

2. The sensor of claim 1 wherein the means for sensing blood pressure comprises a transducer.

3. The sensor of claim 2 further including a flexible diaphragm spaced from the transducer.

4. The sensor of claim 3 further including interface means coupled between the transducer and the flexible diaphragm for transmitting blood pressure pulse signals from the underlying artery to the transducer.

5. The sensor of claim 4 wherein the interface means comprises a fluid coupling medium.

6. The sensor of claim 1 wherein each blood pressure pulse exerts a force on the sensor in a direction parallel to the underlying artery as each pulse crosses an edge of the sensor, and wherein the spacing means further includes means for dampening the force parallel to the underlying artery.

7. The sensor of claim 1 wherein the tissue surrounding the underlying artery exerts a force as the underlying artery is compressed, and wherein the variable height side wall further includes means for neutralizing the force exerted by the tissue proximate the underlying artery.

8. The sensor of claim 1 wherein the side wall is compressible.

9. A sensor for sensing blood pressure within an underlying artery, the sensor comprising:

an external pressure transducer for sensing blood pressure pulses of the underlying artery, the transducer having a sensing surface;

a flexible diaphragm spaced from the sensing surface; and interface means coupled between the sensing surface of the transducer and the flexible diaphragm for transmitting the blood pressure pulses within the underlying artery from the flexible diaphragm to the sensing surface of the transducer; and means for dampening forces in a direction parallel to the underlying artery which are exerted by the blood pressure pulses on the sensor.

10. The sensor of claim 9 wherein the interface means comprises a fluid coupling medium.

11. The sensor of claim 10 wherein the means for dampening comprise a compressible side wall surrounding sensing surface of the transducer and supporting the flexible diaphragm.

12. The sensor of claim 11 wherein the side wall is constrained from expanding parallel to the sensing surface of the transducer.

13. The sensor of claim 11 wherein the side wall is made of foam.

14. The sensor of claim 9 further including means for applying a variable hold down pressure to the sensor.

15. The sensor of claim 14 wherein the means for applying a variable hold down pressure to the sensor comprises:
a base plate;
means for supporting the base plate with reference to the underlying artery;
movable coupling means for movably coupling the sensor to the base plate; and
means for moving the moveable coupling means so that a variable hold down pressure is applied to the sensor.

16. The sensor of claim 14 wherein the means for applying a variable hold down pressure to the sensor comprises:
a base plate;
means for supporting the base plate with reference to the underlying artery;
an outer sleeve coupled to the base plate;
a threaded inner sleeve rotatably supported within the outer sleeve;
a threaded screw shaft coupled to the sensor, the screw shaft slidably engaging the base plate and threadably engaging the inner sleeve so that rotation of the inner sleeve causes the screw shaft to move the sensor up and down to vary the hold down pressure of the sensor; and
a motor for rotating the inner sleeve to vary hold down pressure of the sensor.

17. The sensor of claim 9 further including means for calculating blood pressure based upon the sensed pressure pulses within the underlying artery.

18. The sensor of claim 17 wherein the means for calculating comprise:
a microprocessor for receiving signals representing the sensed blood pressure pulses and the hold down pressure applied to the underlying artery and for calculating blood pressure based upon the received signals representing the blood pressure pulses and the hold down pressures.

19. The sensor of claim 9 further including means for mounting the sensor above the underlying artery.

20. The sensor of claim 19 wherein the means for mounting comprises:
a frame coupled to the sensor, the frame including a stabilizing support protruding from the frame and supporting the frame above the underlying artery; and
a flexible strap coupled to the frame and extending below the underlying artery.

21. A sensor for sensing blood pressure in an underlying artery surrounded by tissue, the sensor comprising:

a transducer element for sensing blood pressure pulses within the underlying artery;
a compressible wall distant from the transducer element, wherein the compressible wall dampens and absorbs forces exerted upon the wall in a direction parallel to the underlying artery and neutralizes forces exerted by the tissue proximate the underlying artery;
a flexible diaphragm supported by the compressible wall and constrained from tension, wherein the compressible wall and the flexible diaphragm at least partially define a chamber in communication with the transducer element; and
a pressure coupling medium within the chamber, whereby the transducer element senses blood pressure pulses transmitted across the flexible diaphragm and through the pressure coupling medium when the flexible diaphragm is placed over the underlying artery.

22. A blood pressure monitoring system for continuous external measurements of blood pressure in an underlying artery surrounded by tissue of a patient, the system comprising:
a sensor for sensing blood pressure pulses in the underlying artery;
means for applying a variable hold down pressure to the sensor;
means for calculating blood pressure based upon the sensed pressure pulses within the underlying artery; and
means for neutralizing forces exerted by the tissue proximate the underlying artery while conforming to the anatomy of the patient.

23. The system of claim 22 wherein the sensor includes:
a transducer having a sensing surface;
a flexible diaphragm for being positioned over the underlying artery;
interface means between the flexible diaphragm and the sensing surface of the transducer for transmitting pressure pulses from the diaphragm to the transducer; and
flexible means for supporting the flexible diaphragm above the underlying artery and for conforming to the anatomy of the patient.

24. The system of claim 23 wherein the interface means comprises a fluid.

25. The system of claim 23 wherein the flexible means for supporting comprises a semi-rigid side wall encircling the interface means and supporting the flexible diaphragm.

26. The system of claim 25 wherein the semi-rigid side wall comprises foam.

27. The system of claim 22 wherein the means for applying the variable hold down pressure to the sensor comprises:
a base plate;
an outer sleeve coupled to the base plate;
a threaded inner sleeve rotatably supported within the outer sleeve;
bearings between the inner sleeve and the outer sleeve for rotatably supporting the inner sleeve relative to the outer sleeve;
a threaded screw shaft coupled to the sensor, the screw shaft slidably engaging the base plate and threadably engaging the inner sleeve so that rotation of the inner sleeve causes the screw shaft to move the sensor up and down to vary the hold down pressure of the sensor; and
a motor for rotating the inner sleeve to vary hold down pressure of the sensor.

28. The system of claim 27 further including means for controlling the motor to control the hold down pressure applied to the sensor.

29. The system of claim 22 wherein the means for calculating blood pressure based upon sensed pressure pulses comprises:

a microprocessor for receiving data representing the sensed pressure pulses and the hold down pressures applied to the underlying artery and for calculating blood pressure based upon the received data representing the pressure pulses and the hold down pressures.

30. The system of claim 22 further including means for mounting the sensor above the underlying artery.

31. The system of claim 30 wherein the means for mounting comprises:

a frame coupled to the sensor, the frame including a stabilizing support protruding from the frame and supporting the frame above the underlying artery; and a flexible strap coupled to the frame and extending below the underlying artery so that the underlying artery is positioned between the flexible strap and the stabilizing support of the frame.

32. The system of claim 31 further including:

a socket coupled to the frame; and a ball coupled to the outer sleeve and frictionally set within the socket for properly orienting the sensor with respect to the underlying artery.

33. The system of claim 22 further including:

means for dampening and absorbing forces exerted by the blood pressure pulses in directions not perpendicular to the underlying artery.

34. An apparatus for sensing blood pressure pulses within an underlying artery surrounded by tissue as the underlying artery is compressed, the apparatus comprising:

a transducer;

a flexible diaphragm for placement above the underlying artery;

a flexible compressible sidewall distant from the transducer and positioned for engaging tissue adjacent the underlying artery; and a fluid coupling medium coupled between the transducer and the flexible diaphragm, wherein the fluid coupling medium transmits blood pressure pulse signals from the underlying artery to the transducer.

35. A sensor for sensing blood pressure within an artery surrounded by tissue, the sensor comprising:

a transducer;

a flexible diaphragm;

a fluid coupling medium coupled between the flexible diaphragm and the transducer; and a compressible wall supported above the artery to at least partially surround the artery and to engage tissue proximate the artery.

36. In a sensor for sensing blood pressure within an underlying artery of a patient, the sensor having a transducer for sensing blood pressure of each pulse as each pulse travels beneath the sensor, an improvement comprising:

a flexible sidewall spaced from the transducer for engaging the tissue and capable of conforming to the anatomy of the patient.

37. In the sensor of claim 36, the improvement further including:

a flexible diaphragm spaced from the transducer; and the fluid coupling medium coupled between the flexible diaphragm and the transducer.

38. For use in a system for non-invasively determining the intraarterial blood pressure of an artery surrounded by tissue, a sensing apparatus comprising:

a compressible sidewall for engaging tissue at least partially surrounding the underlying artery;

a transducer having a sensing surface spaced from the sidewall;

a flexible diaphragm for transmitting blood pressure pulses of the underlying artery; and a fluid coupling medium between the sensing surface of the transducer and the flexible diaphragm.

39. A sensor for sensing blood pressure pulses within an underlying artery surrounded by tissue of a patient as the underlying artery is compressed, the sensor comprising:

a transducer;

a flexible diaphragm for placement above the underlying artery;

a fluid coupling medium coupled between the transducer and the flexible diaphragm for transmitting blood pressure pulse signals from the underlying artery to the transducer; and a flexible sidewall distinct from the transducer and positioned for engaging tissue proximate the underlying artery while being capable of conforming to the anatomy of the patient.

40. The sensor of claim 39 wherein the flexible sidewall is compressible.

41. A sensor for sensing blood pressure pulses within an underlying artery surrounded by tissue as the underlying artery compressed, the sensor comprising:

a transducer;

a flexible diaphragm for placement above the underlying artery;

a variable height body conforming side wall positioned adjacent the flexible diaphragm for engaging tissue proximate to the underlying artery; and a fluid coupling medium between the transducer and the flexible diaphragm, wherein the fluid coupling medium transmits blood pressure pulse signals from the underlying artery to the transducer.

42. A sensor for sensing blood pressure within an artery of a patient, the sensor comprising:

a fluid filled sensing chamber having a diaphragm and a body conforming side wall; and a pressure transducer fluidly coupled to the fluid filled sensing chamber.

43. The sensor of claim 42 further including:

means for positioning the fluid filled sensing chamber and the diaphragm over the artery of the patient.

44. The sensor of claim 42 including:

means for applying a variable hold down pressure to the sensor.

45. A sensor for sensing blood pressure within an artery of a patient, the sensor comprising:

a fluid filled sensing chamber having a diaphragm;

a transducer fluidly coupled to the fluid filled sensing chamber, wherein the transducer senses fluid pressure within the chamber; and a body conformable wall proximate the sensing chamber for applying force to the artery while preventing pressure in a direction generally parallel to the artery from being applied to the sensing chamber.

* * * * *

UNITED STATES PATENT AND TRADEMARK OFFICE
CERTIFICATE OF CORRECTION

PATENT NO. : 5,649,542

DATED : JULY 22, 1997

INVENTOR(S) : G. KENT ARCHIBALD, TIMOTHY G. CURRAN, ORLAND H. DANIELSON, MARIUS O. POLIAC, ROGER C. THEDE

It is certified that error appears in the above-indentified patent and that said Letters Patent is hereby corrected as shown below:

Col. 6, line 16, delete "threes", insert --forces--

Col. 6, line 61, delete "like", insert --free--

Col. 7, line 6, delete "Transducer", insert --transducer--

Col. 7, line 9, delete "force, a", insert --forces--

Col. 7, line 15, delete "arc", insert --are--

Col. 7, line 18, delete "arc", insert --are--

Col. 7, line 35, delete "ground", insert --grounding--

Col. 7, line 57, delete "remote"

Col. 7, line 62, delete "prevent", insert --permit--

Col. 8, line 28, delete ".After", insert --,inner--

Col. 8, line 38, delete second occurrence "to"

Col. 9, line 7, delete second occurrence "of"

Col. 9, line 30, delete "137", insert --132--

UNITED STATES PATENT AND TRADEMARK OFFICE
CERTIFICATE OF CORRECTION

PATENT NO. : 5,649,542
DATED : July 22, 1997
INVENTOR(S) : G. Kent Archibald, et. al.

It is certified that error appears in the above-identified patent and that said Letters Patent is hereby corrected as shown below:

Col. 11, line 10, after "surrounding", insert --the--

Signed and Sealed this

Twenty-third Day of December, 1997

*Attest:*

*Attesting Officer*

BRUCE LEHMAN

*Commissioner of Patents and Trademarks*